United States Patent [19]
Mizuguchi et al.

[11] Patent Number: 5,520,917
[45] Date of Patent: May 28, 1996

[54] MATERIALS IN THE FORM OF COLORED SPHERICAL FINE PARTICLES

[75] Inventors: Masaaki Mizuguchi, Ashiya; Hiroko Ohbayashi, Nishinomiya; Akira Matsueda; Tsuyoshi Ogihara, both of Kawaguchi, all of Japan

[73] Assignees: Suzuki Yushi Industries Co., Ltd., Osaka; Kose Corp., Tokyo, both of Japan

[21] Appl. No.: 89,504

[22] Filed: Jul. 21, 1993

[30] Foreign Application Priority Data

Jul. 27, 1992 [JP] Japan .................................. 4-220679
Sep. 10, 1992 [JP] Japan .................................. 4-269762

[51] Int. Cl.⁶ .............................. A61K 6/00; A61K 7/00
[52] U.S. Cl. ............................................ 424/401; 424/489
[58] Field of Search ........................ 424/401, 70, 69; 106/504

[56] References Cited

U.S. PATENT DOCUMENTS

| | | | |
|---|---|---|---|
| 5,167,709 | 12/1992 | Shinohara et al. | 106/504 |
| 5,196,186 | 3/1993 | Omatsu et al. | 424/63 |
| 5,314,683 | 5/1994 | Schlossman | 424/64 |

*Primary Examiner*—Thurman K. Page
*Assistant Examiner*—William E. Benston, Jr.
*Attorney, Agent, or Firm*—Armstrong, Westerman, Hattori, McLeland & Naughton

[57] ABSTRACT

A colored particulate material in the form of almost perfectly spherical fine particles comprising an organic and/or inorganic pigment coated with a hydrated metal compound over the surface thereof, the coated pigment being enclosed with an inorganic porous wall substance, process for producing the same, and a cosmetic composition comprising the same.

10 Claims, 3 Drawing Sheets

MATERIALS IN THE FORM OF COLORED SPHERICAL FINE PARTICLES

BACKGROUND OF THE INVENTION

1. Field of the Invention

The present invention relates to materials in the form of colored spherical fine particles, processes for producing the same and cosmetic compositions containing the particulate material, and more particularly to materials in the form of colored spherical line particles comprising a porous inorganic wall substance enclosing an organic and/or inorganic pigment therewith, processes for producing these particulate materials and cosmetic compositions containing the material.

2. Description of the Prior Art

It is already well known to prepare inorganic porous spherical fine particles by the so-called interface reaction process. Methods have also been proposed of producing colored fine particles having a coloring agent enclosed therein utilizing this interface reaction process.

In the case where the interface reaction process is utilized and also in the case where a wall substance is prepared from a sol by gelation, the coloring agent needs to be dispersed in an aqueous solution of inorganic electrolyte or in an aqueous solution of metal oxide sol. When dispersed as it is at this time, the coloring agent flocculates and encounters difficulty in forming a uniform dispersion, or repels water because of hydrophobicity, remaining totally unwet and failing to make a dispersion.

Accordingly, it has been proposed to coat the coloring agent with a water-soluble high-molecular-weight organic substance before use to reduce the water repellency of the agent as disclosed in Japanese Patent Laid-open (Ko-kai) Nos. 293028/1991 and 180243/1989.

However, the use of the high-molecular-weight organic substance in this method entails the drawback that the organic substance is thermally affected to discolor when the coated agent is dried by heating, or becomes degraded or decays during storage.

Japanese Patent Laid-open(Ko-kai) No. 81012/1985, for example, discloses a technique for causing silica gel to enclose a coloring agent therein without resorting to the interface reaction process. Since this method does not utilize the interface reaction process, the product obtained has none of the features or advantages of the porous particulate material prepared by the interface reaction process. In the case where the coloring agent is an organic pigment, the pigment becomes degraded and discolored thermally, while when the agent is an inorganic pigment such as an inorganic hydroxide or carbonate pigment, the pigment tends to be decomposed to undergo a color change undesirably.

On the other hand, the beautifying effects of cosmetic compositions, especially those of makeup compositions, chiefly include a skin color correcting effect to conceal defects such as blemishes and birthmarks on the skin and a coloring effect to give attractive features. For cosmetics to exhibit these effects, heretofore used are pigments including titanium dioxide, zinc oxide and like white pigments, iron oxide red, yellow iron oxide, black iron oxide, ultramarine, Prussian blue and like inorganic coloring pigments, and tar pigments and like organic coloring pigments. These pigments are generally particulate or acicular, differ in surface properties, measure about 0.001 to about 1 micrometer in particle size and are accordingly great in the cohesive force or adhesive force of particles although satisfactory in tinting strength and hiding power, so that when incorporated into makeup compositions, they are likely to cause color irregularities and exhibit poor spreadability and an unnatural finish when the composition is applied. To overcome these problems, such pigments are used in combination with extender pigments in the form of globular or platelike particles as components of makeup compositions, or it has recently been attempted to use composite pigments prepared from such a pigment and mica, talc, silica gel, polyamide powder or like extender pigment so as to condition the composition for use, whereas satisfactory pigments still remain to be developed.

Further to provide cosmetic compositions which exhibit an enhanced coloring effect and give an improved feel, for example, as to spreadability when applied, a colored finely particulate silica gel is proposed which is in the form of porous spherical particles containing 1 to 40 wt. % of water-insoluble coloring agent as enclosed in their voids (Examined Japanese Patent Publication No. 28605/1986), but this silica gel is not fully satisfactory with respect to the hiding power. When incorporated into skin care compositions and other cosmetic compositions, the silica gel excessively absorbs sebum from the skin to entail the problem of toughening the skin.

Further processes are known for preparing a powder comprising capsules having a pigment enclosed therein (Examined Japanese Patent Publication Nos. 6251/1979 and 55454/1982), whereas since the pigment enclosure ratio is not sufficient, permitting the enclosed pigment to form flocs, the pigment fails to produce a brilliant color and to exhibit the desired hiding power. Moreover, the powder, which is relatively large in particle size, produces poor beautifying effects with respect to tinting strength and hiding power and presents a rough surface over the skin when used as a component of cosmetic compositions, hence problems. The conventional processes further fail to encapsulate tar pigments and like organic pigments.

SUMMARY OF THE INVENTION

An object of the present invention is to provide a method of producing a material in the form of spherical fine particles having a coloring pigment enclosed therein by the interface reaction process or by preparing a gel from an aqueous solution of metal oxide sol.

Another object of the invention is to overcome the foregoing drawbacks of conventional cosmetic compositions of the type described, and more particularly to provide a makeup composition which produces a vivid color free from irregularities and suitable beautifying effects as in respect of tinting strength and hiding power and which is smoothly spreadable when applied and excellent in sustained beautifying effects such as retention of the color without dulling despite lapse of time.

The first object can be fulfilled by using a pigment which affords a uniform dispersion when admixed with the aqueous solution of electrolyte or the aqueous solution of metal oxide sol, more particularly by using an organic or inorganic pigment coated with a hydrated metal compound over the surface for producing colored spherical fine particles having the pigment enclosed therein by the interface reaction process or a process wherein a gel is prepared from the aqueous solution of metal oxide sol.

The other object of the invention is attained by incorporating into a cosmetic composition the above colored particulate material as it is or as treated with an oily substance or fluorine-containing resin.

DETAILED DESCRIPTION OF THE INVENTION

Figure 1:
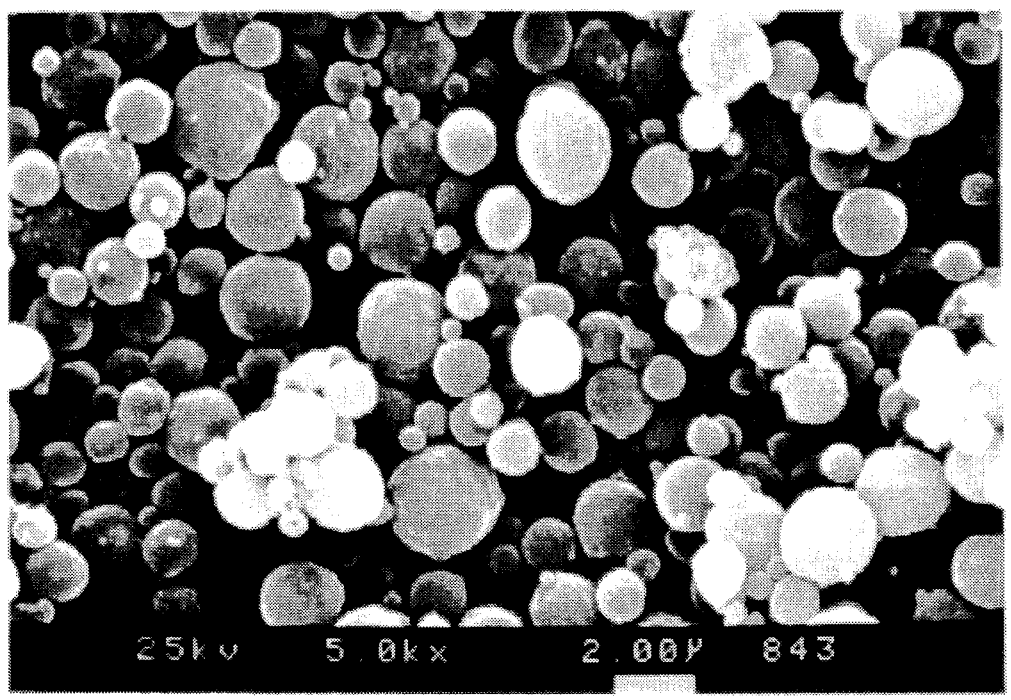
FIG. 1 is a scanning electron photomicrograph (X5,000) of spherical fine particles of Example 1.

Generally, the present invention provides materials in the form of colored spherical fine particles, processes for producing such materials and cosmetic compositions containing the particulate material. The processes will be described first, followed by a description of colored particulate materials and then by a description of cosmetic compositions.

The pigments to be used in the present invention include inorganic and organic pigments which are such that when the pigment is dispersed as it is in an aqueous solution of inorganic electrolyte or aqueous solution of metal oxide sol, (a) the pigment flocculates and encounters difficulty in making a uniform dispersion, or (b) the pigment is difficult to wet with water and repels water because of hydrophobicity, encountering difficulty in forming a dispersion as already described. While pigments are rendered hydrophobic by a treatment and thereby prevented from flocculating when dried during production, the pigment to be used in the invention can be a hydrophobic pigment thus treated, or a pigment as made into a slurry or paste with water.

The inorganic electrolyte is not limited specifically. Examples of useful electrolytes are all of those usually termed as such, and are typically sodium silicate, potassium silicate, ammonium silicate, sodium carbonate, potassium carbonate, etc. Examples of useful metal oxide sols are sols of metal oxides such as silica, alumina, zirconia, titanium dioxide, barium oxide, zinc oxide and iron oxide.

Examples of typical pigments for use in the present invention are as follows.

Inorganic Pigments

White pigments: titanium dioxide, zinc oxide, lithopone, zinc sulfide, zirconium oxide, barium metaborate, Pattinson white, manganese white, tungsten white, magnesium oxide, etc.

Black pigments: carbon black, iron black, titanium black, silica black, graphite, etc.

Gray pigments: zinc dust, zinc carbide, etc.

Red pigments: iron oxide red, cobalt red, molybdenum red, cobalt magnesia red, cuprous oxide, copper ferrocyanide, Yellow pigments: ocher, iron oxide yellow, titanium yellow, barium yellow, strontium yellow, chrome titanium yellow, aureolin (cobalt yellow), tungsten yellow, vanadium yellow, nickel yellow, etc.

Green pigments: chrome green, chromic oxide, chromic hydroxide, zinc green, cobalt green, cobalt-chrome green, Egyptian green, manganese green, Bremen green, titanium green, etc.

Blue pigments: ultramarine, Prussian blue, cobalt blue, tungsten blue, molybdenum blue, Egyptian blue, Bremen blue, copper borate, lime blue, Violet pigments: Mars violet, manganese violet, cobalt violet, cobalt violet, chromic chloride, copper violet, ultramarine violet, etc.

Metal powder pigments: aluminum powder, copper powder, bronze powder, stainless steel powder, nickel powder, silver powder, gold powder, etc.

Brown pigments: umber, iron oxide powder, Vandyke brown, Prussian brown, manganese brown, copper brown, cobalt brown, Pearl pigments: titanated mica, fish scale white, bismuth oxychloride, titanated mica treated with iron oxide, mica titanium treated with Prussian blue, titanated mica treated with carbon black, titanated mica treated with carmine, etc.

Other pigments: silica, silica white, calcium carbonate, barium carbonate, magnesium carbonate, magnesium silicate, calcium silicate, barium sulfate precipitated, baryte, alumina white, talc, gypsum, clay, satin white, bentonite, magnesia, slaked lime, strontium white, kaolin, mica, sericite, etc.

Organic Pigments

Organic pigments are shown in Table 1 below.

TABLE 1

| Kind | Color Index Number | Color Index Name | United State Name | European Community Name |
| --- | --- | --- | --- | --- |
| Red | 15850:1 | Pigment Red 57:1 | D and C Red No. 7 | 15820[3] |
| Red | 15585 | Pigment Red 53 | — | 15585 |
| Red | 15585:1 | Pigment Red 53:1 | — | 15585[3] |
| Red | 15630:2 | Pigment Red 49:2 | — | 15630 |
| Red | 15630:1 | Pigment Red 49:1 | — | 15630 |
| Red | 15630:3 | Pigment Red 49:3 | — | 15630 |
| Red | 45170 | Basic Violet 10 | — | — |
| Red | 45410:1 | Solvent Red 48 | D and C Red No. 27 | 45410 |
| Red | 15880:1 | Pigment Red 63:1 | D and C Red No. 34 | 15880[3] |
| Red | 45380:2 | Solvent Red 43 | D and C Red No. 21 | 45380 |
| Red | 15800:1 | Pigment Red 64:1 | D and C Red No. 31 | 15800 |
| Red | 73360 | Vat Red 1 | D and C Red No. 30 | 73360 |
| Red | 12085 | Pigment Red 4 | D and C Red No. 36 | 12085 |
| Red | 12120 | Pigment Red 3 | — | 12120 |
| Red | 12315 | Pigment Red 22 | — | — |
| Red | 15865 | Pigment Red 48 | — | 15865 |

TABLE 1-continued

| Kind | Color Index Number | Color Index Name | United State Name | European Community Name |
|---|---|---|---|---|
| Red | 15630 | Pigment Red 49 | — | — |
| Red | 26105 | Solvent Red 24 | — | — |
| Orange | 45370:1 | Solvent Red 72 | D and C Orange No. 5 | 45370 |
| Orange | 12075 | Pigment Orange 5 | — | — |
| Orange | 21110 | Pigment Orange 13 | — | — |
| Orange | 45425:1 | Solvent Red 73 | D and C Orange No. 10 | 45425 |
| Orange | 11725 | Pigment Orange 1 | — | 11725 |
| Yellow | 45350:1 | Acid Yellow 73 | D and C Yellow No. 7 | 45350 |
| Yellow | 47000 | Solvent Yellow 33 | D and C Yellow No. 11 | 47000 |
| Yellow | 21090 | Pigment Yellow 12 | — | — |
| Yellow | 11680 | Pigment Yellow 1 | — | 11680 |
| Green | 61570 | Acid Green 25 | D and C Green No. 5 | 61570 |
| Green | 61565 | Solvent Green 3 | D and C Green No. 6 | 61565 |
| Blue | 73000 | Vat Blue 1 | — | 73000 |
| Blue | 69825 | Vat Blue 6 | — | 69825 |
| Blue | 74160 | Vat Blue 15 | — | 74160 |
| Violet | 60725 | Solvent Violet 13 | D and C Violet No. 2 | 60725 |

These pigments are used singly, or at least two of them are use in admixture.

According to the present invenion, the pigment is coated with a hydrated metal oxide. The hydrated metal oxide is silica, alumina, zirconia, titanium dioxide, barium oxide or iron oxide, among which silica or alumina is preferred. Although it is as a rule desirable to form the coating of hydrated metal oxide over the entire surface of the pigment nearly uniformly, satisfactory results can be achieved if at least 30%, preferably at least 80%, of the surface of the pigment is coated. The coating has a thickness at least not smaller than that of a single-molecule layer and not permitting flocculation of the primary particles of the pigment. Preferably, the thickness is approximate to that of two-to three-molecule layer.

The method of coating the pigment with the hydrated metal oxide is not limited specifically insofar as the above-mentioned coating can be formed as specified. Typically such coatings are formed, for example, by the following methods.

(A) A method comprising adding the pigment to an alkoxy metal compound or alcohol solution thereof, stirring the mixture with a stirrer such as an ultrasonic dispersing machine or high-speed stirrer to prepare a uniform dispersion and adding water and a hydrolysis catalyst to the dispersion to hydrolyze the alkoxy metal compound and deposit a hydrated metal oxide on the surface of the pigment.

Examples of typical alkoxy metal compounds for use in this method are those represented by the general formula $M(OR)_n$ wherein M is a metal element, R is alkyl and n is a formula weight. M is preferably Si, Al, Zr, Ba, Ti or the like. R is usually alkyl having 1 to 8 carbon atoms, preferably 1 to 3 carbon atoms.

The alcohol to be used is one capable of dissolving the alkoxy metal compound. Such alcohols are not only monohydric ones but also dihydric or tri-hydric alcohols, preferred examples being methanol, ethanol, isoproyl alcohol, glycerin, etc. The alcohol solution is usually about 5 to about 30% in concentration. The hydrolysis catalyst is a usual one, such as HCl or $NH_4OH$, and is used in an amount of about 0.1 to about 1%.

(B) A method comprising adding the pigment to an alcohol to wet the surface of the pigment therewith with stirring, treating the mixture by a suitable stirrer such as an ultrasonic dispersing machine or high-speed stirrer to prepare a uniform dispersion, mixing an aqueous solution of metal oxide sol with the dispersion and adding an acidic substance, basic substance or electrolyte to the mixture to cause the metal oxide sol to gel and deposit a hydrated metal oxide on the surface of the pigment for coating.

Alcohols usable in this method are the same as those exemplified for use in the method (A). The acidic substance to be used is usually hydrochloric acid, sulfuric acid, phosphoric acid or the like. The basic substance to be used is usually sodium hydroxide, potassium hydroxide, ammonia or the like. Useful electrolytes and metal oxide sols are the same as those previously mentioned in connection with pigments.

(C) A method comprising adding the pigment to an alcohol solution of mixture of a metal oxide sol and an alkoxy metal compound, stirring the mixture to wet the surface of the pigment with the solution, treating the mixture with a suitable stirrer such as an ultrasonic dispersing machine or high-speed stirrer to prepare a uniform dispersion and adding an acidic substance, basic substance or electrolyte to the dispersion to cause the metal oxide sol to gel and deposit a hydrated metal oxide on the surface of the pigment, whereby the pigment surface is coated with the hydrated metal oxide.

The metal oxide sol, alkoxy metal compound, alcohol, acidic substance, basic substance and electrolyte to be used in this method can be those for use in the above method (A) or (B).

According to the invention, the pigment thus coated with the hydrated metal compound can be enclosed with a porous inorganic wall substance by the known so-called interface reaction process or a process for converting a sol to a gel disclosed, for example, in Japanese Patent Laid-open No. 103904/1989, whereby colored spherical fine particles are obtained.

When the interlace reaction process is resorted to, the colored particulate material is prepared, for example, by a process which comprises (i) dispersing the coated pigment in an aqueous solution containing at least one inorganic compound selected from among alkali metal silicates, carbonates, phosphates and sulfates, and alkaline earth metal halides and nitrates, (ii) admixing an organic solvent having a solubility of up to 8% in water with the resulting dispersion to obtain a W/O emulsion, and (iii) admixing with the emulsion an aqueous solution of at least one compound selected from among alkaline earth metal halides, inorganic acids, organic acids, inorganic acid ammonium salts, organic acid ammonium salts and alkali metal carbonates and capable of forming a water-insoluble precipitate by an aqueous solution reaction with the inorganic compound. Alternatively, the aqueous solution of compound used in the step (iii) is admixed with the dispersion resulting from the step (i) before admixing the organic solvent with the dispersion.

This process can be practiced, for example, by the procedures disclosed in Examined Japanese Patent Publication No. 6251/1979 or No. 55454/1982.

Stated more specifically, an aqueous solution is prepared which contains at least one inorganic compound selected from among alkali metal silicates, carbonates, phosphates and sulfates, and alkaline earth metal halides and nitrates at a concentration of 0.3 mole/liter to saturation.

An organic solvent having a solubility preferably of up to 8% in water is then admixed with the dispersion prepared by the step (i) to obtain a W/O emulsion.

With 100 parts by weight of this W/O emulsion is thereafter admixed 100 to 2,000 parts by weight of an aqueous solution (0.05 mole/liter to saturation, preferably 0.1 to 2.0 moles/liter, in concentration) of at least one compound selected from among alkaline earth metal halides, inorganic acids, organic acids, inorganic acid ammonium salts, organic acid ammonium salts, alkali metal carbonates and capable of forming a water-insoluble precipitate by an aqueous solution reaction with the abovementioned inorganic compound.

Examples of preferred organic solvents having a solubility of up to 8% in water are as follows.

Aliphatic hydrocarbons: n-Hexane, isohexane, n-heptane, isoheptane, n-octene, isooctene, gasoline, petroleum ether, kerosene, benzine, mineral spirit, etc.

Alicyclic hydrocarbons: Cyclopentane, cyclohexane, cyclohexene, cyclononane, etc.

Aromatic hydrocarbons: Benzene, toluene, xylene, ethylbenzene, propylbenzene, cumene, mesitylene, Tetralin, styrene, etc.

Ethers: Propyl ether, isopropyl ether, etc.

Halogenated hydrocarbons: Methylene chloride, chloroform, ethylene chloride, trichloroethane, trichloroethylene, etc.

Esters: Ethyl acetate, n-propyl acetate, isopropyl acetate, n-amyl acetate, isoamyl acetate, butyl lactate, methyl propionate, ethyl propionate, butyl propionate, methyl butyrate, ethyl butyrate, butyl buyrate, etc.

These organic solvents are usable singly, or at least two of them can be used in mixture.

The W/O emulsion to be prepared is 4/1 to 1/5, preferably about 2/1 to about 1/2, in W/O ratio. The amount of surfactant to be used is preferably up to about 10 wt. %, more preferably about 0.1 to about 3 wt. % based on the organic solvent.

The surfactant to be used is a nonionic surfactant. Examples of preferred surfactants are as follows.

Polyoxyethylene sorbitan fatty acid esters: Polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, polyoxyethylene sorbitan stearate, etc.

Polyoxyethylene higher alcohol ethers: polyoxyethylene lauryl ether, polyoxyethylene cetyl ether, polyoxyethylene stearyl ether, polyoxyethylene oleyl ether, polyoxyethylene octyl phenol ether, polyoxyethylene nonyl phenol ether, etc.

Polyoxyethylene fatty acid esters: Polyoxyethylene glycol monolaurate, polyoxyethylene glycol monostearate, polyoxyethylene glycol stearate, polyoxyethylene glycol monooleate, etc.

Glycerin fatty acid esters: Stearic acid monoglyceride, oleic acid monoglyceride, etc.

Polyoxyethylene sorbitol fatty acid esters: Polyoxyethylene sorbitol tetraoleate, etc.

Among these surfactants, polyoxyethylene sorbitan fatty acid esters are especially preferable. These surfactants are used singly, or at least two of them are used in admixture.

A typical example of method of converting the sol to a gel is disclosed in Japanese Patent Laid-open No. 103904/1989. The gelation can be effected advantageously by the method described in detail in the publication.

The pigment for use in the process of the invention has a coating of hydrated metal oxide formed before use, so that when added to the aqueous solution of step (i) of the interface reaction process or to the sol of the above publication No. 103904/1989, the pigment exhibits very high dispersibility, giving a uniform dispersion. For this reason, the present process for producing the desired colored particulate material has the following advantages.

1. The pigment is entirely enclosed.

2. The pigment is uniformly dispersed within the enclosing particles and is enclosed apparently in the form of flocs, whereas the pigment is dispersed within the enclosing particles while remaining primary particles and therefore exhibits higher brightness.

3. The pigment is treated with a hydrated metal compound, i.e., hydrated inorganic compound, thereafter enclosed with an inorganic compound, and therefore improved in heat resistance and durability.

4. If pigments which are different in surface characteristics are mixed together, they gather together or repel each other and are liable to cause a color separation. However, when surface-treated with the same hydrated inorganic oxide, even different pigments assume the same surface condition and become readily amenable to the enclosing treatment.

5. The pigment can be made into a uniform dispersion. This makes it possible to easily and reliably prepare a W/O emulsion having very small liquid droplets when the pigment is to be enclosed. Consequently, the colored particulate material obtained is in the form of very fine spherical particles to exhibit further increased brightness as a coloring pigment.

6. Since the pigment can be made into a uniform dispersion, the pigment is usable at a high concentration, consequently affording a coloring material of high enclosure ratio.

This enables the particulate material obtained to exhibit a bright color and great tinting strength.

7. When pigments are surface-modified with a surfactant, the surfactant is separated from the pigment surface. As the result, pigment-enclosing particles are not obtained. On the other hand, in the present invention, the above drawbacks never occur.

8. When the material obtained is incorporated into cosmetic compositions, the pigment which is coated with an inorganic substance is held out of direct contact with the skin and therefore unlikely to be adsorbed by the skin or to penetrate into the skin. This obviates the likelihood of the pigment causing contact dermatitis or cutaneous disorders.

Additionally, the fine particles obtained are spherical and accordingly highly smooth-surfaced.

If the original pigment, which is uncoated, is used as it is in the present process, the following phenomena will result.

1. Some of the pigment only is enclosed, with many pigment particles remaining unenclosed, and the pigment produces a very thin whitish color and dissolves out, for example, while the particles obtained are washed.

2. Since flocculating particles are enclosed, the pigment produces a color tone of very large particles, failing to exhibit the inherent color tone of primary particles. Even ii enclosed, therefore, the pigment shows a dull dark color.

3. When the pigment is not enclosed effectively but remains bare, or is coated with an organic high-molecular-weight material, the advantage of the present invention is not available.

4. Pigments of different surface characteristics, if mixed together, will flocculate or repel each other to cause a color separation. The different pigments will not be enclosed in the same particle, failing to exhibit the contemplated color.

The colored particulate material of the present invention has the following features.

(i) The material is in the form of fine particles usually about 0.1 to about 50 micrometers in size.

(ii) The fine particles are nearly spherical.

(iii) The particles comprise a coloring pigment enclosed with a wall substance which is porous and inorganic.

(iv) The wall substance is usually about 0.05 to about 25 micrometers in thickness.

The cosmetic composition of the present invention will be described next.

Basically, the cosmetic composition of the invention has incorporated therein the colored particulate material, as further treated with an oily substance or fluorine-containing resin when so required.

The colored particulate material to be incorporated into the desired cosmetic composition of the invention will be further described.

The colored particulate material to be used to give a sufficient tinting strength and hiding power is usually 0.1 to 50 micrometers in particle size, preferably 1 to 5 micrometers in mean particle size. The ratio of inorganic pigment and/or organic pigment to be enclosed is 10 to 60 wt. % based on the whole weight of colored particulate material. If the enclosure ratio is less than 10 wt. %, the concentration of pigment(s) to be enclosed is too low to give a sufficient tinting strength or hiding power and is undesirable. Enclosure ratios in excess of 60% are in no way advantageous industrially.

The cosmetic composition of the invention may have incorporated therein the colored particulate material as it is or as treated with an oily substance or fluorine-containing resin. This treatment assures the desired cosmetic composition of sustained beautifying effects such as color retention without dulling despite lapse of time and effectively prevents the composition from roughening the skin. The oily substance to be used for the treatment is any of those usually used for cosmetic composition, such as liquid paraffin, squalane, Vaseline, paraffin wax, microcrystalline wax, beeswax, candelilla wax, rhodinic acid pentaerythritol ester, dimethylpolysiloxane and methylhydrogenpolysiloxane.

Other compounds for treating the colored particulate material to be incorporated into the cosmetic composition of the invention are fluorine-containing resins such as Teflon and fluoroalkylphosphoric acid ethanolamine salts represented by the following formulae. Commercial products of such ethanolamine salts include AG530 (product of Asahi Glass Co., Ltd).

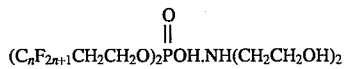  Formula 1

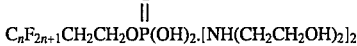  Formula 2

In the above formulae, n is an integer of 6 to 18.

The method of treatment is not limited in any way but can be a suitably selected one, and typically comprises, for example, adding water to the colored particulate material or to a mixture of at least two such materials to obtain a slurry, slowly admixing with the slurry an emulsion which is prepared by adding water to a fluoroalkyl-containing compound and stirring the mixture and which has a concentration of 0.1 to 5 wt. %, rendering the resulting emulsion acidic, breaking down the emulsion as by allowing it to stand at room temperature or high temperature to coat the surface of the particles with a continuous layer of the fluoroalkyl-containing compound, and subsequently washing, filtering off and drying the particles. The concentration of the slurry to be used is not limited specifically. Even when having a high concentration, for example, of 5 to 20 wt. %, the slurry can be thoroughly stirred for mixing and treated in a large quantity by a small device. The fluoroalkyl-containing compound is used preferably in an amount of 0.1 to 10 wt. %, more preferably 0.5 to 5 wt. %, based on the particles. The treatment can be carried out at an atmospheric temperature of 10° to 35° C.

The cosmetic composition of the present invention has incorporated therein the colored particulate material in an amount of 0.1 to 50 wt. % based on the whole weight of the composition. If the amount is less than 0.1 wt. %, a sufficient effect will not be obtained, whereas amounts in excess of 50 wt. % are not desirable not only because the effect then remains unchanged and also because the cosmetic composition is not usable to give a wide variety of impressions, or is lower in impact strength when in the form of a press-molded powdery product.

The cosmetic composition of the present invention is available in various forms such as powdery, liquid, solid or gel forms. Such compositions are usable as skin care compositions including pack, sun care milk, lotion and body powder compositions, and makeup compositions including face powder, foundation, eye shadow, blush, lipstick, eye liner and eye brow compositions.

Besides the colored particulate material, various additives which are usually used for cosmetics can be incorporated as suitably selected into the present composition insofar as they do not impair the advantages of the invention. Examples of such additives are inorganic pigments, organic pigments, gelling agents, surfactants, lower alcohols, polyhydric alcohols, purified water, preservatives, antioxidants, ultraviolet absorbers, humectants, beautifying components, perfumes, etc.

The cosmetic composition of the invention having the colored particulate material incorporated therein produces a vivid color free from irregularities, exhibits beautifying effects such as a suitable tinting strength and hiding power and effects to block ultraviolet rays such as an antisunburn effect, is smoothly spreadable when applied and will not roughen the skin. When the present composition is a makeup composition, the composition forms a cosmetic coating which appears natural on finishing and exhibits greatly sustained beautifying effects such as color retentivity free of dulling despite lapse of time.

The colored particulate material of the present invention is useful not only for cosmetic compositions but also for color printer toners, copying toners, coating compositions, printing inks, correction inks, leads of color pencils and aqueous or oily marking inks and as additives for resins and coloring agents for pharmaceutical products.

EXAMPLES

The present invention will be described in greater detail with reference to the following examples and comparative examples, in which percentages are by weight.

Example 1

Into a 100-ml Erlenmeyer flask of Teflon were placed 18.7 g of tetraethoxysilane and 10 g of ethanol, and 4.5 g of a commercial hydrophobic pigment, i.e., Color Index No. 11680 (Hanza Yellow) was placed into the flask and wetted with and disperesed in the mixture by an ultrasonic dispersing machine.

A 0.8 ml quantity of 1N hydrochloric acid serving as a hydrolyzing agent for the tetraethoxysilane was added to the dispersion, and the mixture was heated in a thermostatic chamber at 60° C. for 30 minutes while being treated by the machine to deposit fine particles of silica on the surface of the pigment.

Ion exchange water (80 ml) was added to the dispersion thus obtained, followed by stirring, 90 ml of a solution of 3 moles/liter of JIS No. 3 sodium silicate was added to the dispersion of Color Index No. 11680, followed by thorough mixing, and the mixture was added to 500 ml of a solution of 20 g/liter of sorbitan monostearate in toluene, followed by stirring at 10,000 r.p.m. for 1 minute to obtain a W/O emulsion.

The emulsion was added to 1300 ml of an aqueous solution of 2.0 moles/liter of ammonium sulfate, and the mixture was stirred for 1 hour for reaction.

The reaction mixture was thereafter filtered, and the solids separated off were washed with water and then with alcohol and dried at 105° C. for 24 hours, giving about 26 g of yellow spherical fine particles of silica having about 17% of Color Index No. 11680 enclosed therein and measuring about 2 micrometers in mean size. FIG. 1 shows a scanning electron photomicrograph of the product.

Example 2

Ethanol (20 g) was placed into a 100-ml Erlenmeyer flask of Teflon, and 4.5 g of a commercial hydrophobic pigment, Color Index No. 73360 (Helindon Pink CN) was added to the ethanol. The pigment was wetted with and dispersed in the ethanol by an ultrasonic dispersing machine.

A 27 g quantity of silica sol ("Snowtex O", product of Nissan Chemical Industries, Ltd.) as adjusted to a pH of 7.0 with ammonia water was added to the dispersion, and the mixture was heated in a themostatic chamber at 60° C. for 5 hours while being treated by the machine to deposit fine particles of silica on the pigment surface.

Ion exchange water (50 ml) was added to the dispersion thus obtained, followed by stirring, 90 ml of a solution of 3 moles/liter of JIS No. 1 sodium silicate was added to the dispersion of Color Index No. 73360, followed by thorough mixing, and the mixture was added to 500 ml of a solution of 30 g/liter of 1:1 mixture of polyoxyethylene (n=4) nonyl phenyl ether and polyoxyethylene (n=9.5) nonyl phenyl ether in n-hexane, followed by stirring at 9,000 r.p.m. for 1 minute to obtain a W/O emulsion.

The emulsion was added to 1,500 ml of an aqueous solution of 2.0 moles/liter of calcium chloride, and the mixture was stirred for 5 hours for reaction and then allowed to stand for 24 hours.

The reaction mixture was thereafter filtered, and the solids separated off were washed with water and then with alcohol and dried at 105° C. for 24 hours, consequently giving about 42 g of red spherical fine particles of calcium silicate having about 10% of Color Index No. 73360 enclosed therein and measuring about 3 micrometers in mean size.

Example 3

Into a 100-ml Erlenmeyer flask of Teflon were placed 27 g of an NTL agent L-2102 (brand name, product of Nissan Chemical Industries, Ltd.), i.e., a mixture of an alkoxylsilane and silica sol, and 10 g of isopropyl alcohol. A 4.5 g quantity of a commercial hydrophobic pigment, Color Index No. 74160 (Phthalocyanine Blue) and 35 g of anatase-type titanium dioxide (brand name, "JA-1", product of Tayca Corporation) were placed into the flask, and wetted with and dispersed in the mixture by an ultrasonic dispersing machine.

The dispersion was heated in a thermostatic chamber at 60° C. for 1 hour while being ultrasonically treated to deposit fine particles of silica on the pigment surface.

Ion exchange water (100 ml) was added to the dispersion thus obtained, followed by stirring, and 90 ml of a solution of 4 moles/liter of JIS No. 1 sodium silicate was added to the dispersion of Color Index No. 74160 and titanium dioxide, followed by thorough mixing.

Dilute sulfuric acid (100 ml) separately prepared was added to the mixture as maintained at a temperature of up to 10° C., and the resulting mixture was added to 500 ml of a solution of 20 g/liter of polyoxyethylene sorbitan trioleate in kerosene with icecooling, followed by stirring at 7,000 r.p.m. for 1 minute to give a W/O emulsion.

The emulsion was maintained at room temperature for 10 minutes and then slowly heated to 50° C. while being stirred at 500 r.p.m., followed by gelation for about 5 hours.

Figure 2:
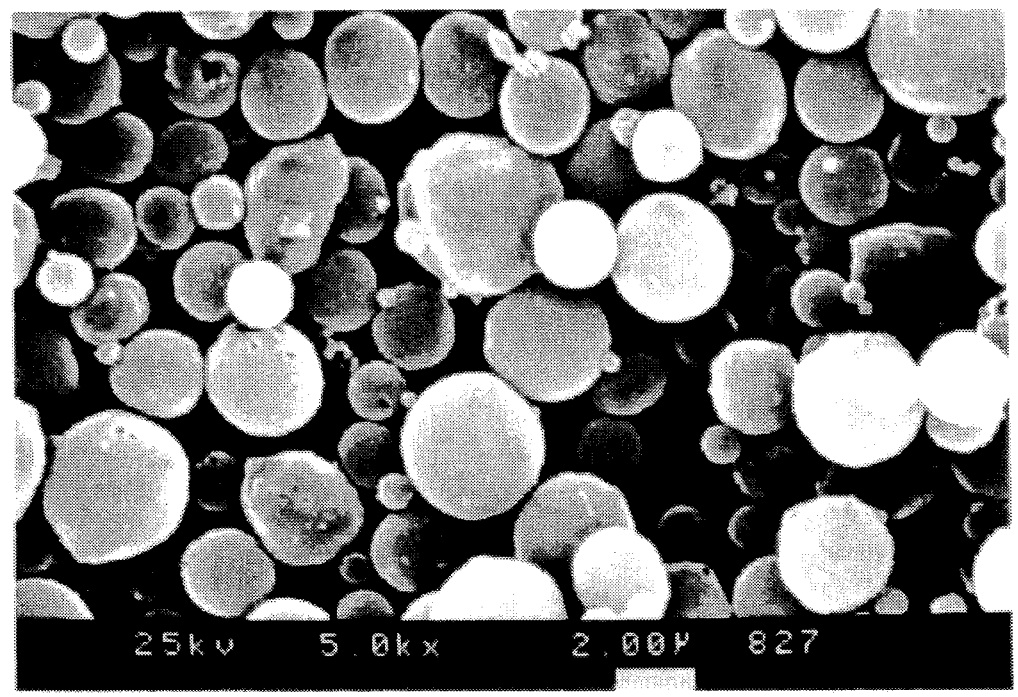
FIG. 2 is a scanning electron photomicrograph (X5,000) of spherical fine particles of Example 3.

The resulting gel was filtered, and the solids separated off were washed with water and then with alcohol and dried at 105° C. for 24 hours, consequently giving about 64 g of blue spherical fine particles of silica having about 6.8% of Color Index No. 74160 and about 54.3% of titanium dioxide enclosed therein and measuring about 5 micrometers in mean size. FIG. 2 shows a scanning electron photomicrograph of the product.

Example 4

Into a 100-ml Erlenmeyer flask of Teflon were placed 11.2 g of tetraethoxysilane, 4.4 g of triisopropyl oxide aluminum and 30 g of isopropyl alcohol, and 2.0 g of Color Index No. 21090 (Benzidine Yellow G) and 2.0 g of Color Index No.15865 (Permanent Red), which are commercial hydrophobic pigments, were placed into the flask and wetted with and dispersed in the mixture by an ultrasonic dispersing machine.

To the dispersion was added 1 ml of 1N ammonia water as a hydrolyzing agent for the tetraethoxysilane and triisopropyl oxide aluminum, and the mixture was heated in a thermostatic chamber at 60° C. for 30 minutes while being treated by the machine to deposit fine silica particles and fine alumina particles (3:1) on the pigment surface.

Ion exchange water (80 ml) was added to the dispersion thus obtained, followed by stirring, 100 ml of a solution of 4 moles/liter of JIS No. 4 sodium silicate was added to the dispersion of Color Index No. 21090 and Color Index No. 15865, followed by thorough mixing, and the mixture was added to 600 ml of a solution of 10 g/liter of 1:2 mixture of polyoxyethylene sorbitan monooleate and sorbitan monopalmitate in a 3:2 mixture of cyclohexane and xylene, followed by stirring at 10,000 r.p.m. for 1 minute to obtain a W/O emulsion.

The emulsion was added to 3,000 ml of an aqueous solution of 1.0 mole/liter of potassium hydrogencarbonate, and the mixture was stirred for 1 hour for reaction.

The reaction mixture was thereafter filtered, and the solids separated off were washed with water and then with alcohol and dried at 105° C. for 24 hours, consequently affording about 33 g of orange spherical fine particles of silica having about 6% of Color Index No. 21090 and 6% of Color Index No. 15865 enclosed therein and measuring about 3 micrometers in mean size.

Example 5

Ethanol (20 g) was placed into a 100-ml Erlenmeyer flask of Teflon, and 2.0 g of a commercial hydrophobic pigment, Color Index No. 11725 (Hanza Orange) and 30 g of iron oxide red were added to the ethanol, and wetted with and dispersed in the ethanol by an ultrasonic dispersing machine.

To the dispersion was added 12 g of silica sol (Snowtex 40) as adjusted to a pH of 7.0 with hydrochloric acid, and the mixture was heated in a thermostatic chamber at 60° C. for 5 hours while being treated by the machine to deposit fine silica particles on the pigment surface.

Ion exchange water (50 ml) was added to the dispersion thus prepared, followed by stirring, 100 ml of a solution of 3 moles/liter of JIS No. 1 sodium silicate was thoroughly admixed with the dispersion of Color Index No. 11725 and iron oxide red, and the mixture was added to 500 ml of a solution of 30 g/liter of a 2:1 mixture of glycerol monostearate and polyoxyethylene (n=9.5) nonyl phenyl ether in xylene. The resulting mixture was stirred at 2,000 r.p.m. for 1 minute, giving a W/O emulsion.

The emulsion was added to 1,500 ml of an aqueous solution of 2.0 moles/liter of calcium chloride, and the mixture was stirred for 5 hours for reaction and allowed to stand for 24 hours.

The reaction mixture was thereafter filtered, and the solids separated off were washed with water and then with alcohol and dried at 105° C. for 24 hours, consequently giving about 71 g of bright orange spherical fine particles of calcium silicate having about 2.8% of Color Index No. 11725 and about 41.9% of iron oxide red enclosed therein and measuring about 30 micrometers in mean size.

Example 6

Into a 100-ml Erlenmeyer flask of Teflon were placed 11.2 g of tetraethoxysilane, 4.4 g of triisopropyl oxide aluminum and 30 g of isopropyl alcohol, and 28 g of commercial futile-type titanium dioxide (brand name, "JR", product of Tayca Corporation) was placed into the flask, and wetted with and dispersed in the mixture by an ultrasonic dispersing machine.

To the dispersion was added 1 ml of 1N ammonia water as a hydrolyzing agent for the tetraethoxysilane and triisopropyl oxide aluminum, and the mixture was heated in a thermostatic chamber at 60° C. for 30 minutes while being treated by the machine to deposit fine silica particles and fine alumina particles (3:1) on the pigment surface.

Ion exchange water (80 ml) was added to the dispersion thus obtained, followed by stirring, 100 ml of a solution of 4 moles/liter of JIS No. 3 sodium silicate was thoroughly admixed with the dispersion of titanium dioxide, and the mixture was added to 500 ml of a solution of 15 g/liter of sorbitan monostearate in toluene, followed by stirring at 11,800 r.p.m. for 1 minute to obtain a W/O emulsion.

The emulsion was added to 3,000 ml of an aqueous solution of 2.0 moles/liter of sodium sulfate, and the mixture was stirred for 1 hour for reaction.

The reaction mixture was thereafter filtered, and the solids separated off were washed with water and then with alcohol and dried at 105° C. for 24 hours, consequently giving about 54 g of white spherical fine silica particles having about 50% of rutile-type titanium dioxide enclosed therein and measuring about 3 micrometers in mean size.

Comparative Example 1

Ethanol (10 g) was placed into a 100-ml Erlenmeyer flask of Teflon, and 4.5 g of a commercial hydrophobic pigment, Color Index No. 11680 (Hanza Yellow) was added to the ethanol, and wetted with and dispersed in the ethanol by an ultrasonic dispersing machine.

A W/O emulsion was prepared by adding 0.8 ml of 1N hydrochloric acid to the dispersion, heating the mixture in a thermostatic chamber at 60° C. for 30 minutes while treating the mixture by the machine, stirring the mixture with addition of 80 ml of ion exchange water, further adding 90 ml of a solution of 3 moles/liter of JIS No. 3 sodium silicate, followed by thorough mixing, adding 500 ml of a solution of 20 g/liter of sorbitan monostearate in toluene as in Example 1 and stirring the resulting mixture at 10,000 r.p.m. for 1 minute.

The emulsion was added to 1,300 ml of an aqueous solution of 2.0 moles/liter of ammonium sulfate, and the mixture was stirred for 1 hour for reaction.

The reaction mixture was thereafter filtered, and the solids separated off were washed with water and then with alcohol and dried at 105° C. for 24 hours, consequently giving spherical silica particles about 2 micrometers in mean size and having enclosed therein little or no Color Index No. 11680.

Accordingly, the product was considerably thinner than that of Example 1 in color.

Comparative Example 2

Into a 100-ml Erlenmeyer flask of Teflon was placed 20 g of isopropyl alcohol, and 4.5 g of a commercial hydrophobic pigment, Color Index No. 74160 (Phthalocyanine Blue) and 35 g of rutile-type titanium dioxide (brand name, "JR", product of Tayca Corporation) were added to the alcohol, and wetted with and dispersed in the alcohol by an ultrasonic dispersing machine.

The dispersion was heated in a themostatic chamber at 60° C. for 1 hour while being treated by the machine, 100 ml of ion exchange water was added to the resulting dispersion, followed by stirring, and 90 ml of a solution of 4 moles/liter of JIS No. 1 sodium silicate was added to the dispersion of Color Index No. 74160 and titanium dioxide, followed by thorough mixing.

The mixture was thereafter treated in the same manner as in Example 3, followed by filtration, washing with water and alcohol and drying at 105° C. for 24 hours.

Figure 3:
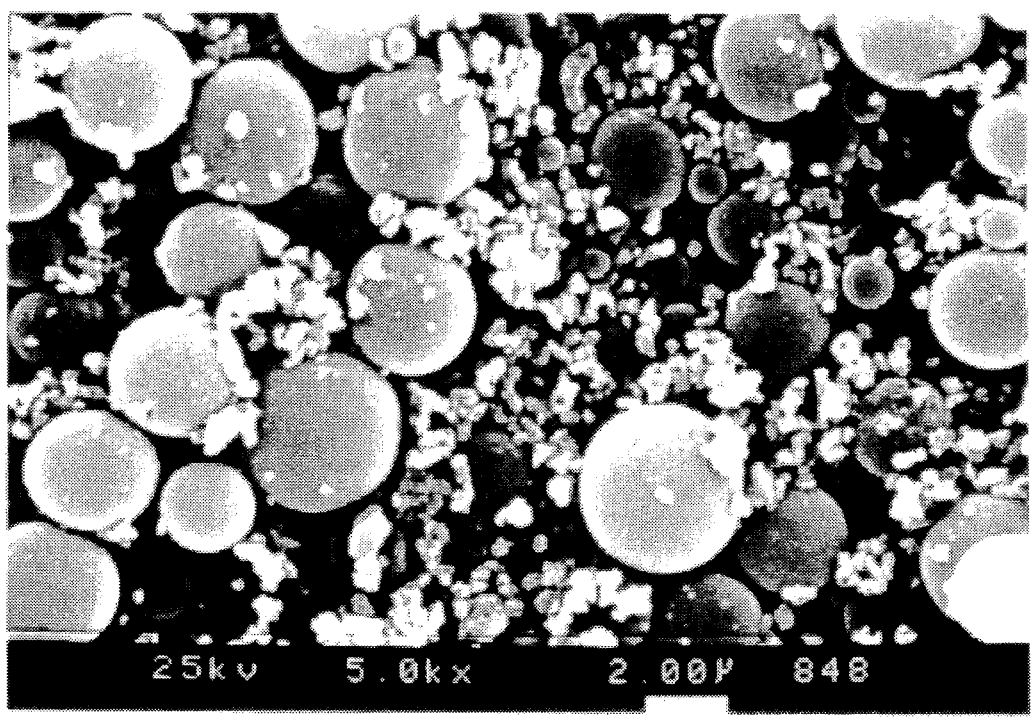
FIG. 3 is a scanning electron photomicrograph (X5,000) of spherical fine particles of Comparative Example 2.

The above treatment should have afforded blue spherical fine particles of silica having about 6.8% of Color Index No. 74160 and about 54.3% of titanium dioxide enclosed therein and measuring about 5 micrometers in mean size, whereas the blue pigment dissolved out during washing to give white spherical particles. FIG. 3 shows a scanning electron photomicrograph of the product.

Example 7

Into a 100-ml Erlenmeyer flask of Teflon were added 18.7 g of tetraethoxysitane and 20 g of ethyl alcohol, and 20 g of titanium dioxide in the form of superfine particles (2 micrometers in mean size) was placed into the flask, and wetted with and dispersed in the mixture by an ultrasonic dispersing machine.

To the dispersion was added 1 ml of 1N ammonia water as a hydrolyzing agent for the tetraethoxysilane, and the mixture was heated in a thermostatic chamber at 60° C. for 30 minutes while being treated by the machine to deposit fine silica particles on the pigment surface.

Ion exchange water (80 ml) was added to the resulting dispersion, followed by stirring, 90 ml of a solution of 3 moles/liter of JIS No. 3 sodium silicate was added to the dispersion of superfine particulate titanium dioxide, followed by thorough mixing, and the mixture was added to a solution of 15 g/liter of sorbitan monostearate in toluene, followed by stirring at 11,800 r.p.m. for 1 minute to obtain a W/O emulsion.

The emulsion was added to 2,000 ml of an aqueous solution of 1.5 moles/liter of sodium sulfate, and the mixture was stirred for 1 hour for reaction.

The reaction mixture was thereafter filtered, and the solids separated off were washed with water and then with alcohol and dried at 105° C. for 24 hours, consequently giving about 43 g of silica capsules having about 50% of superfine particulate titanium dioxide enclosed therein and measuring about 2 micrometers in mean particle size.

Example 8

The white particulate silica (100 parts by weight) obtained in Example 6 was dispersed in a solution of 2 parts by weight of methylhydrogenpolysiloxane in 100 parts by weight of isopropyl alcohol to prepare a slurry, which was then dried in a vacuum with heating for a treatment. The product was pulverized to prepare a white particulate material in the form of spherical fine particles having titanium dioxide enclosed therein, i.e., "(silicone oil-treated) silica capsules enclosing silica-and alumina-deposited titanium dioxide."

Example 9

Water (1,000 ml) was added to 50 parts by weight of the white particulate silica obtained in Example 6 to prepare a slurry. On the other hand, an emulsion was prepared by adding 350 ml of water to 9 g of a fluoroalkylphosphoric acid ester diethanolamine salt (AG530, product of Asahi Glass Co., Ltd.) and stirring the mixture. The emulsion was slowly added to the slurry and mixed therewith, followed by standing at room temperature to obtain (AG530-treated) silica capsules enclosing silica-alumina-deposited titanium dioxide.

For use in Examples 10 to 16 given below, colored particulate materials in the form of fine spherical particles were prepared in the same manner as in Examples 6, 7 and 8.

Example 10

A powder foundation, shown in Table 2, was prepared and evaluated with respect to the beautifying effects, spreadability on application and sustained beautifying effects.

Method of Evaluation

A sensory test was conducted by a panel of 20 experts to evaluate the foundation in seven grades ranging in score from 1 point for a very low effect to 7 points for a very high effect. The average scores gained were expressed according to the following criteria.

Criteria

⊚: at least 6 points.
○: at least 4 points to below 6 points
Δ: at least 2 points to below 4 points
X: below 2 points

Preparation Process

No. 1 to No. 11 were mixed together and pulverized, No. 12 to No. 15 melted by heating were mixed with and dispersed in the mixture, and the resulting mixture was homogenized by pulverization and pressmolded in specified containers.

TABLE 2

| No. | Component | Ex. 1 | Comparative Example 1 | 2 | 3 |
|---|---|---|---|---|---|
| 1 | Titanium dioxide | 5.0 | 15.0 | 5.0 | 5.0 |
| 2 | Titanium dioxide capsules (Note 1) | 20.0 | — | — | — |
| 3 | Titanium dioxide capsules (Note 2) | — | — | 0.0 | — |
| 4 | Titanium dioxide capsules (Note 3) | — | — | — | 20.0 |
| 5 | Particulate silica (average particle diameter is 3 μm) | — | 10.0 | — | — |
| 6 | Talc | 15.0 | 15.0 | 15.0 | 15.0 |
| 7 | Sericite | 39.4 | 39.4 | 39.4 | 39.4 |
| 8 | Iron oxide red | 0.8 | 0.8 | 0.8 | 0.8 |
| 9 | Iron oxide yellow | 1.5 | 1.5 | 1.5 | 1.5 |
| 10 | Iron oxide black | 0.2 | 0.2 | 0.2 | 0.2 |
| 11 | Titanated mica | 3.0 | 3.0 | 3.0 | 3.0 |
| 12 | Squalane | 8.0 | 8.0 | 0 | 8.0 |
| 13 | Petrolatum | 2.0 | 2.0 | 2.0 | 2.0 |
| 14 | Dimethlypolysiloxane (20CS) | 5.0 | 5.0 | 5.0 | 5.0 |
| 15 | Perfume | 0.1 | 0.1 | 0.1 | 0.1 |
| | (Evaluation) | | | | |
| | Natural finish | ⊚ | X | ○ | ○ |
| | Sustained beautify effect | ⊚ | ⊚ | X | Δ |
| | Spreadability when applied | ⊚ | Δ | ⊚ | ⊚ |
| | Lasting effect | ⊚ | Δ | ○ | X |

Note 1: (Silicone oil-treated) silica capsules enclosing silica-deposited titanium dioxide (enclosure ratio 50%, mean particle size 3 micrometers) of Example 8
Note 2: (Silicone oil-treated) silica capsules enclosing titanium dioxide (enclosure ratio 10%, mean particle size 10 micrometers)
Note 3: (Silicone oil-treated) silica capsules enclosing silica-deposited titanium dioxide (enclosure ratio 50%, mean particle size 60 micrometers)

Example 11

| Two- Way Foundation | Amount (%) |
|---|---|
| 1. Silica capsules enclosing silica-deposited titanium dioxide (enclosure | 10.0 |

| Two-Way Foundation | | Amount (%) |
|---|---|---|
| | ratio 45%, mean particle size 2 μm) | |
| 2. | Titanium dioxide | 8.0 |
| 3. | Finely particulate titanium dioxide (P-25) | 5.0 |
| 4. | Mica | 31.4 |
| 5. | Talc | 10.0 |
| 6. | Titanated Mica | 10.0 |
| 7. | Iron oxide red | 0.4 |
| 8. | Iron oxide yellow | 2.0 |
| 9. | Iron oxide black | 0.2 |
| 10. | Spherical polystyrene particles | 5.0 |
| 11. | Methylhydrogenpolysiloxane (Shin-Etsu Silicone KF-99) | 2.0 |
| 12. | Dimethylpolysiloxane (Shin-Etsu Silicone KF-96(100CS)) | 5.0 |
| 13. | Microcrystalline wax | 1.0 |
| 14. | Liquid paraffin | 5.0 |
| 15. | Beeswax | 0.5 |
| 16. | Glyceryl trioctanoate | 3.0 |
| 17. | UV absorber | 1.0 |
| 18. | Antioxidant | 0.1 |
| 19. | Preservative | 0.3 |
| 20. | Perfume | 0.1 |

Preparation Process

1. No. 1 to No. 9 were mixed together and pulverized.

2. No. 11 and No. 12 were dissolved in isopropyl alcohol, the mixture 1 was added to the solution to obtain a slurry, and the slurry was dried in a vacuum with heating, and thereafter pulverized.

3. The pulverized product 2 and No. 10 were mixed together, No. 13 to No. 20 as melted by heating were admixed with the mixture, and the resulting mixture was pulverized for homogenization.

4. The mixture 3 was press-molded in a specified metal tray.

Evaluation

The two-way foundation of Example 11 was applicable with dry sponge or sponge wet with water, smoothly spreadable when applied to produce a uniform finish and exhibit a suitable skin color modifying effect and excellent in sustained beautifying effects, retaining its color free of dulling despite lapse of time.

Example 12

| Solid Foundation | | Amount (%) |
|---|---|---|
| 1. | (Rhodinic acid pentaerythritol ester-treated) silica capsules enclosing silica-deposited titanium dioxide and iron oxide red (titanium dioxide 48%, iron oxide red 2%, paricle size 3 μm) | 30.0 |
| 2. | Titanium dioxide | 5.0 |
| 3. | Titanated Mica | 3.0 |
| 4. | Sericite | 3.0 |
| 5. | Talc | 3.9 |
| 6. | Nylon powder (SP-500) | 8.0 |
| 7. | Iron oxide red | 0.3 |
| 8. | Iron oxide yellow | 3.5 |
| 9. | Iron oxide black | 0.3 |
| 10. | Dextrin fatty acid ester | 2.5 |
| 11. | Carnauba wax | 2.0 |
| 12. | Paraffin wax | 3.5 |
| 13. | Dimethylpolysiloxane (Shin-Etsu Silicone KF-96(6CS)) | 10.0 |
| 14. | Methylphenylpolysiloxane | 5.0 |

| Solid Foundation | | Amount (%) |
|---|---|---|
| | (Shin-Etsu Silicone KF-56) | |
| 15. | Liquid paraffin | 8.5 |
| 16. | Glyceryl trioctanoate | 10.0 |
| 17. | UV absorber | 1.0 |
| 18. | Antioxidant | 0.1 |
| 19. | Preservative | 0.3 |
| 20. | Perfume | 0.1 |

Preparation Process

1. No. 1 to No. 9 were mixed together and pulverized.

2. No. 10 to No. 20 were melted by heating, the material 1 was added to the mixture and the resulting mixture was homogenized by a roll mill.

3. The mixture 2 was melted by heating and defoamed in a vacuum.

4. The mixture 3 was melted by heating, poured into a specified tray.

Evaluation

The solid foundation of the invention was smoothly spreadable when applied to produce a uniform finish and a suitable skin color modifying effect and excellent in sustained beautifying effects.

Example 13

| Makeup Base Component | | Amount (%) |
|---|---|---|
| 1. | Stearic acid | 2.0 |
| 2. | Cetanol | 1.0 |
| 3. | Glycerin fatty acid ester | 1.0 |
| 4. | Sorbitan sesquioleate | 0.6 |
| 5. | Polyoxyethylene sorbitan trioleate (20 E.O.) | 1.0 |
| 6. | Liquid paraffin | 5.0 |
| 7. | Paraffin wax | 5.0 |
| 8. | Decamethylpentacyclosiloxane | 3.0 |
| 9. | Triethanolamine | 2.0 |
| 10. | Glycerin | 3.0 |
| 11. | Purified water | 54.2 |
| 12. | Carboxyvinyl polymer | 0.2 |
| 13. | 1,3-Butylene glycol | 14.0 |
| 14. | (Glyceryl trioctanoate-treated) silica capsules enclosing silica-deposited titanium dioxide and Color Index No.74160 (54% titanium dioxide and 6% Color Index No. 74160 in enclosure ratio, 5 μm in mean particle size) | 1.0 |
| 15. | Iron oxide yellow | 0.2 |
| 16. | Talc | 3.8 |
| 17. | Soybean lecithin | 0.2 |
| 18. | Polyoxyethylene sorbitan monooleate (20 E.O.) | 0.8 |
| 19. | Ethyl alcohol | 1.8 |
| 20. | Preservative | 0.1 |
| 21. | Perfume | 0.1 |

Preparation Process

1. No. 13 to 18 were made into a homogeneous dispersion by a roll mill.

2. No. 12 was added to No. 11 for swelling, No. 9, No. 10 and the dispersion 1 were added to the swollen polymer, and the mixture was made into a dispersion by mixing.

3. No. 1 to No. 8 were melted by heating and adjusted to 70° C., and the dispersion 2 as similarly adjusted to 70° C. was slowly added to the mixture with stirring to obtain an emulsion, which was then cooled to 40° C.

4. No. 19 to No. 21 as made into a solution were admixed with the emulsion 3.

5. The mixture 4 was filled into a tube to obtain a makeup base.

Evaluation

The makeup base of the invention had a vivid color and suitable control effect, exhibited good spreadability when applied, did not roughen the skin and sustained the effects of foundation cosmetics.

Example 14

| Rouge Component | Amount (%) |
| --- | --- |
| 1. Talc | 30.0 |
| 2. Titanated mica | 10.0 |
| 3. Mica | 43.4 |
| 4. Calcium silicate capsules enclosing silica-deposited Color Index No. 73360 (enclosure ratio 10%, mean particle size 3 μm) | 5.0 |
| 5. Ultramarine | 2.0 |
| 6. Microcrystalline wax | 0.5 |
| 7. Squalane | 5.0 |
| 8. Petrolatum | 1.0 |
| 9. Dimethylpolysiloxane (Shin-Etsu Silicone KF-96 (100CS)) | 3.0 |
| 10. Perfume | 0.1 |

Preparation Process

1. No. 1 to No. 5 were mixed together and pulverized.

2. No. 6 to No. 10 as melted by heating were admixed with the pigment 1, followed by pulverization to obtain a homogeneous mixture.

3. The mixture 2 was press-molded in a specified tray to obtain a rouge.

Evaluation

The rouge of the invention had a suitable tinting strength, exhibited good spreadability when applied, produced a vivid color, gave a natural finish, retained its color without dulling despite lapse of time and was excellent in sustained beautifying effects.

Example 15

| Pack Component | Amount (%) |
| --- | --- |
| 1. Vinyl acetate resin emulsion | 15.0 |
| 2. Polyvinyl alcohol | 10.0 |
| 3. Glycerin | 5.0 |
| 4. (Teflon-treated) silica capsules enclosing silica-and alumina-deposited titanium dioxide (enclosure ratio 45%, mean particle size 30 μm) | 14.0 |
| 5. (Teflon-treated) silica capsules enclosing silica-and alumina-deposited Color Index No. 21090 and Color Index No. 73360 (6% Color Index No. 21090 and 6% Color Index No. 73360 in enclosure ratio, mean particle size 3 μm) | 1.0 |
| 6. Zinc oxide | 5.0 |
| 7. Kaolin | 5.0 |
| 8. Ethyl alcohol | 5.0 |
| 9. Purified water | 39.7 |
| 10. Perfume | 0.2 |
| 11. Preservative | 0.1 |

Preparation Process

1. No. 1 to No. 3 and No. 8 to No. 11 were mixed together into a homogeneous mixture by stirring.

2. No. 4 to No. 7 were added to the mixture 1, followed by kneading to obtain a pack composition.

Evaluation

The pack composition of the invention had a vivid color, was smoothly spreadable when applied, did not roughen the skin and was excellent.

Example 16

| Lipstick Component | Amount (%) |
| --- | --- |
| 1. Ceresin wax | 4.0 |
| 2. Beeswax | 5.0 |
| 3. Candelilla wax | 7.0 |
| 4. Carnauba wax | 2.0 |
| 5. Castor oil | 49.2 |
| 6. Hexadecyl alcohol | 25.0 |
| 7. Titanium dioxide | 2.0 |
| 8. Silica capsules enclosing silica-deposited Color Index No. 73360 (enclosure ratio 22%, mean particle size 2 μm) | 5.0 |
| 9. Silica capsules enclosing silica-deposited Color Index No.11680 (enclosure ratio 17%, mean particle size 2 μm) | 0.7 |
| 10. Perfume | 0.1 |

Preparation Process

1. No. 1 to No. 6 were melted by heating.

2. No. 7 to No. 9 were added to the molten mixture 1, and the resulting mixture was made into a uniform dispersion by a roll mill.

3. A lipstick was prepared by adding No. 10 to the dispersion 2 as melted by heating, then defoaming the mixture, and pouring the mixture in a mold, followed by cooling for solidification.

Evaluation

The lipstick of the invention had a suitable tinting strength, was smoothly spreadable when applied, produced a vivid color free from irregularities and exhibited greatly sustained beautifying effects without the likelihood of its color becoming dull with time.

Example 17

| Powder | | Amount (%) |
| --- | --- | --- |
| 1. | Silica capsules enclosing silica-deposited titanium dioxide[*1] (enclosure ratio 50%, particle size 2 μm) | 50.0 |
| 2. | Talc | 35.9 |
| 3. | Mica | 5.0 |

-continued

| Powder | | Amount (%) |
| --- | --- | --- |
| 4. | Iron oxide red | 0.1 |
| 5. | Iron oxide yellow | 0.4 |
| 6. | Iron oxide black | 0.1 |
| 7. | Methylhydrogenpolysiloxane (Shin-Etsu Silicone KF-99) | 1.0 |
| 8. | Dimethylpolysiloxane (Shin-Etsu Silicone KF-96 (100CS)) | 4.0 |
| 9. | UV absorber | 3.0 |
| 10. | Antioxidant | 0.1 |
| 11. | Preservative | 0.3 |
| 12. | Perfume | 0.1 |

[1]: Finely particulate titanium dioxide, MT-500B, product of Tayca Corporation

Preparation Process

1. No. 1 to No. 6 were mixed together and pulverized.

2. No. 7 and No. 8 were dissolved in n-hexane, and the material 1 was added to the solution to obtain a slurry, which was then dreid by heating in a vacuum, and thereafter pulverized.

3. The resulting product 2 was mixed with No. 9 to No. 12, and the mixture was pulverized to obtain a homogeneous mixture.

4. The mixture 3 was filled into a specified container.

Evaluation

Figure 4:
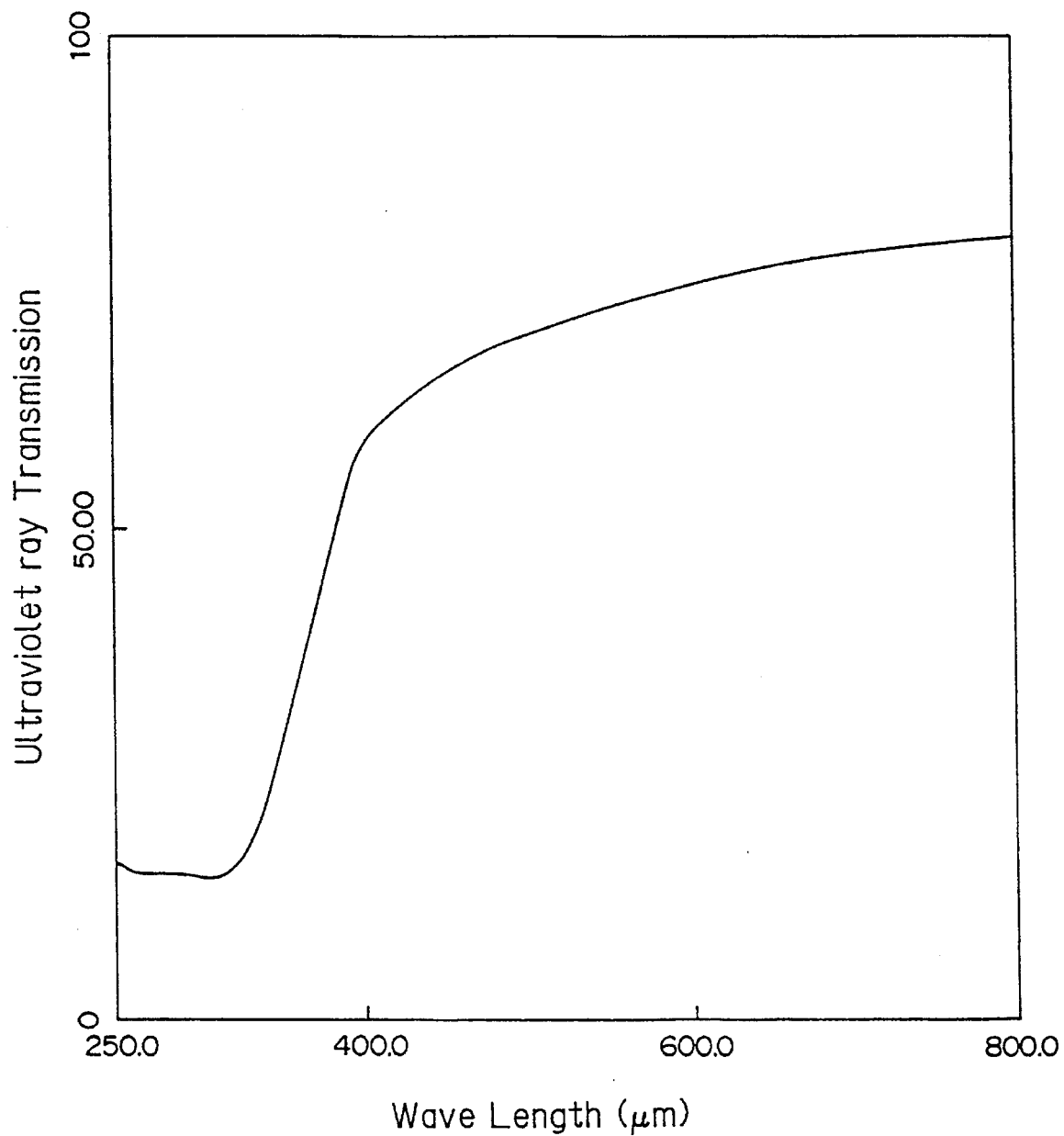
FIG. 4 is a graph showing the UV ray transmittance of the product of Example 17.

The powder of the invention achieved a high effect to block ultraviolet rays (FIG. 4), was smoothly spreadable when applied to give a uniform finish, had a natural matting effect and hiding power and further exhibited greatly sustained beautifying effects without becoming dull with time.

What we claim is:

1. A process for producing colored spherical fine particles comprising adding an organic or inorganic pigment coated with a hydrated metal compound to an aqueous solution containing at least one inorganic compound selected from the group consisting of alkali metal silicates, carbonates, and phosphates, and alkaline earth metal halides and nitrates to obtain a dispersion, and admixing with the dispersion with an aqueous solution of at least one compound selected from the group consisting of alkaline earth metal halides, inorganic acids, organic acids, inorganic acid ammonium salts, organic acid ammonium salts and alkali metal carbonates and capable of forming a water-insoluble precipitate by an aqueous solution reaction with the inorganic compound, before or after admixing the dispersion with an organic solvent having a solubility of up to 8% in water to obtain a W/O emulsion.

2. A process for producing colored spherical fine particles comprising adding an organic or inorganic pigment coated with a hydrated metal compound to a metal oxide sol or a sol mixture comprising the metal oxide sol and an inorganic compound, or alkoxide, mixing the resulting mixture with a water-insoluble or sparingly water-soluble organic solvent in the presence of a surfactant to form a W/O sol emulsion, mixing the emulsion with a basic substance or electrolyte to cause the sol forming the aqueous layer of the emulsion to gel to obtain spherical gel particles, and subsequently heating the particulate gel to remove the water in the gel from the system as a mixture with the organic solvent.

3. A process as defined in claim 1 or 2 wherein the coated organic or inorganic pigment is prepared by adding a pigment to an alkoxy metal compound or an alcohol solution thereof, stirring the mixture to wet the surface of the pigment, subsequently forming the mixture into a uniform dispersion, and hydrolyzing the alkoxy metal compound by adding water and a hydrolyzing catalyst to the dispersion to deposit a hydrated metal oxide on the pigment surface for coating.

4. A process as defined in claim 1 or 2 wherein the coated organic or inorganic pigment is prepared by adding a pigment to an alcohol, stirring the mixture to wet the surface of the pigment, forming the mixture into a uniform dispersion, mixing an aqueous solution of metal oxide sol with the dispersion, and adding at least one of an acid, a base and electrolyte to the resulting mixture to cause the metal oxide sol to gel and deposit a hydrated metal oxide on the pigment surface for coating, the acid being selected from the group consisting of hydrochloric acid, sulfuric acid and phosphoric acid, and the base being selected from the group consisting of sodium hydroxide, potassium hydroxide and ammonia.

5. A process as defined in claim 1 or 2 wherein the coated organic or inorganic pigment is prepared by adding a pigment to an alcohol solution of mixture of a metal oxide sol and an alkoxy metal compound, stirring the resulting mixture to wet the surface of the pigment, forming the mixture into a uniform dispersion, and adding at least one of an acid a base electrolyte to the dispersion to cause the metal oxide sol to gel and deposit a hydrated metal oxide on the pigment surface for coating.

6. A cosmetic composition comprised of colored almost perfectly spherical fine particles comprising an organic pigment and/or an inorganic pigment coated with a hydrated metal compound over the surface thereof, the coated pigment or pigments being enclosed with a porous layer of inorganic material, the colored almost perfectly spherical particles being prepared by a process comprising adding an organic or inorganic pigment coated with a hydrated metal compound to an aqueous solution containing at least one inorganic compound selected from the group consisting of alkali metal silicates, carbonates, and phosphates, and alkaline earth metal halides and nitrates to obtain a dispersion, and admixing with the dispersion with an aqueous solution of at least one compound selected from the group consisting of alkaline earth metal halides, inorganic acids, organic acids, inorganic acid ammonium salts, organic acid ammonium salts and alkali metal carbonates and capable of forming a water-insoluble precipitate by an aqueous solution reaction with the inorganic compound, before or after admixing the dispersion with an organic solvent having a solubility of up to 8% in water to obtain a W/O emulsion.

7. A cosmetic composition as defined in claim 6 wherein the particles are 0.1 to 50 micrometers in size.

8. A cosmetic composition as defined in claim 6 wherein the particles are treated with at least one oily substance selected from the group consisting of liquid paraffin, squalene, Vaseline, paraffin wax, microcrystalline wax, beeswax, candelilla wax, rhodinic acid, pentaerythritol ester, dimethyl polysiloxane and methylhydrogenpolysiloxane, or at least one fluorine-containing resin selected from the group consisting of Teflon and fluoroalkylphosphoric acid ethanolamine salts.

9. A colored particulate material according to claim 6, wherein the inorganic material of the porous layer comprises at least one member selected from the group consisting of alkali metal silicates, carbonates, phosphates and sulfates, and alkaline earth metal halides and nitrates.

10. A colored particulate material as defined in claim 6, wherein the hydrated metal compound is selected from the group consisting of silica, alumina, zirconia, titanium dioxide, barium oxide and iron oxide.

\* \* \* \* \*